United States Patent [19]

Theis et al.

[11] Patent Number: 4,525,310

[45] Date of Patent: Jun. 25, 1985

[54] METHOD OF PREPARING 3-ALKOXY ACRYLONITRILES

[75] Inventors: Christoph Theis, Bornheim; Uwe Prange, Niederkassel, both of Fed. Rep. of Germany

[73] Assignee: Dynamit Nobel AG, Troisdorf, Fed. Rep. of Germany

[21] Appl. No.: 467,053

[22] Filed: Feb. 16, 1983

[30] Foreign Application Priority Data

Feb. 26, 1982 [DE] Fed. Rep. of Germany ....... 3206878

[51] Int. Cl.³ .......................................... C07C 121/453
[52] U.S. Cl. .................................................. 260/465.6
[58] Field of Search ........................... 260/465.6, 465 F

[56] References Cited

U.S. PATENT DOCUMENTS 4,228,097 10/1980 El-Chahawi et al. ....... 260/465.6 X
4,319,024 3/1982 Peeters et al. ............... 260/465.6 X

*Primary Examiner*—Joseph Paul Brust
*Attorney, Agent, or Firm*—Felfe & Lynch

[57] ABSTRACT

3-Alkoxy acrylonitriles are obtained directly from the corresponding nitriles by reaction of carbon monoxide and alcoholates followed by reaction with organic halides.

8 Claims, No Drawings

METHOD OF PREPARING 3-ALKOXY ACRYLONITRILES

BACKGROUND OF THE INVENTION

The invention relates to a method of preparing 3-alkoxy acrylonitriles by the reaction of a substituted or unsubstituted aliphatic nitrile with carbon monoxide and metal alcoholates at elevated pressure and temperature, followed by alkylation with an organic halide.

In the state of the art, alpha-formyl alkali salts and alkaline earth salts can be prepared from the nitriles in accordance with DE-OS No. 2,753,322. In a separate reaction in accordance with DE-OS No. 2,912,345, these salts can form 3-alkoxy acrylonitriles. The performance of the two reactions one after the other with, as a rule, different solvents and adjuvants is difficult and results in losses of material.

It is therefore the object of the present invention to prepare 3-alkoxy acrylonitriles by a method that is simple to practice.

BRIEF DESCRIPTION

The object is achieved in accordance with the invention by reacting substituted or unsubstituted aliphatic nitriles with carbon monoxide and alcoholate and, without isolating the alpha-formyl alkali or alkaline earth salts of the nitriles, the product is formed by reaction with substances of the formula $R^3$-Hal.

DESCRIPTION OF THE PREFERRED EMBODIMENTS

The invention is concerned with a method for preparing 3-alkoxyacrylonitriles of the formula $$R^3O-CH=C-C\equiv N, \qquad I$$
$$\quad\quad\quad\quad\quad |$$
$$\quad\quad\quad\quad R^1$$

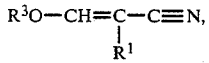

wherein $R^1$ has the meaning H, straight-chain or branched alkyl moieties of 1 to 20 carbon atoms, straight-chain or branched moieties $-(CH_2)_n-CN$, $-(CH_2)_nOR^4$ or $-(CH_2)_n-CH(OR^4)_2$ with the meaning $n=0$ to 5, $R^4$ is alkyl and Cyc=isocyclic or heterocyclic, mono- or polynuclear aromatic or cycloaliphatic ring systems which bear in some cases substituents on the rings; and wherein $R^3$ has the meaning of straight-chain or branched alkyl or alkenyl moieties with 1 to 12 carbon atoms, isocyclic or heterocyclic, mono- or polynuclear aromatic or cycloaliphatic ring systems, which in some cases bear substituents, or $-(CH_2)_p-Cyc$ with Cyc in the previous meaning, the moieties $-(CH_2)_p-OR^4$ with $p=1$ to 5 as well as $R^4$ in accordance with the previous meaning; characterized in that an aliphatic nitrile of the formula $$R^1-CH_2-CN \qquad II,$$

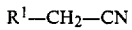

wherein $R^1$ has the same meaning as above, is reacted with an alcoholate of the formula $$M(OR^2)m \qquad III,$$

wherein M is an alkali metal with $m=1$ or an alkaline earth metal with $m=2$ and $R^2$ is a straight-chain or branched alkyl moiety of 1 to 5 carbon atoms, and with carbon monoxide at elevated pressure and temperature to form the corresponding alpha-formyl alkali or alkaline earth salt of compound II, and this salt, without the need for further treatment of the resulting reaction mixture, is reacted at elevated temperature with a halogen compound of the formula $$R^3\text{-Hal} \qquad IV,$$

wherein $R^3$ has the above-given meaning and Hal represents chlorine, bromine or iodine.

In a greatly preferred embodiment of the method, the nitrile of Formula II serves as starting substance and as solvent. This method of procedure operates with very low consumption of carbon monoxide because of a suppression of side reactions.

In working up the product it is therefore possible simply to separate a mixture of formic acid ester, alcohol, residues of the halide $R^3$-Hal and the excess nitrile by distillation without fractionation, and this mixture is then reusable.

Alkali or alkaline earth alcoholates can be used as the alcoholates of formula III. Sodium and potassium salts of methanol or ethanol are preferred for practical reasons of easy availability.

It is greatly preferred to perform the reaction in the presence of a basically reacting compound of the alkali or alkaline earth metals. For example, alkali or alkaline earth hydroxides, hydrogen carbonates, carbonates or oxides, preferably $Ca(OH)_2$, can be used.

The basically reacting compound is used in a ratio of 0.05 to 1 equivalent, preferably 0.4 to 0.6 equivalents, for each mole of alcoholate. To increase selectivity and yield it is furthermore greatly preferred to use tertiary amines or quaternary ammonium bases as catalysts. The tertiary amines can contain identical, or in some cases different, linear or branched cycloalkyl, aralkyl or alkyl moieties of 1 to 20 carbon atoms. Of the cyclic moieties, monocyclic moieties are preferred, and of the aliphatic moieties those of 1 to 6 carbon atoms are preferred.

The quaternary ammonium salts can contain the named moieties or aryl or aralkyl moieties and a monovalent anion. Of the cyclic moieties, monocyclic are preferred, and of the aliphatic moieties those of 1 to 6 carbon atoms are preferred.

Preferred catalysts are trimethylamine, triethylamine and tetra-n-butylammonium chloride or bromide. The catalysts are added in concentrations of 1 to 10%, preferably 3 to 5%, of the weight of alcoholate used.

The chlorine compounds are preferred as halides of Formula IV. The bromides or iodides, which can also be used, offer no advantages over the chlorine compounds.

The carbon monoxide can be used at pressures from 5 to 100, preferably 10 to 50 bar. Higher pressures are possible, but unnecessary. The carbon monoxide can be mixed with other gases such as nitrogen or hydrogen.

The reaction with the halides takes place between standard pressure and 50 bar, preference being given to standard pressure or a slightly high pressure. The temperature can be between 20° and 220° C. In the reaction with carbon monoxide, temperatures from 35° to 100° C. are preferred. In the reaction with the halides, the preferred temperatures range from 90° to 150° C.

Since the nitriles used as starting materials are also solvents, they are used in such an amount that the reaction mixture can be easily stirred. In general, 5 to 20 moles of nitrile are used per equivalent of the alcoholate. Thus, virtually all of the alcoholate is reacted. The excess of the nitrile surprisingly suppresses, to a great extent, the formation of formic acid esters from the alcohol being released and the carbon monoxide. The consumption of carbon monoxide amounts to only 1.2 to 1.7 mol CO per mole of alcoholate, while at the same time the formic acid ester can be re-used as a source of carbon monoxide.

The halides of formula IV are used in amounts of 1 to 2 moles per equivalent of the alcoholate. The excess halides can be recovered.

All in all, the method results in a considerable saving of materials, energy and time, especially in view of the reusability of the starting substances and adjuvants. All of the starting substances and adjuvants, with the exception of the halides, can be added right at the beginning of the reaction.

It is advantageous that iodides are not necessary in the reaction. The amounts of the basically reacting compounds which have been mentioned are relatively small. Advantageously, only 4 to 6% of C-alkylated products are formed, by weight.

The reaction times, of only 1 to 2 hours, are short, but after the halides are added it is desirable to allow time for the completion of the reaction. At the end of the reaction time, solid components are removed by filtration or centrifugation. Very advantageously, the low-boiling products can first be separated by distillation, and then the product can be separated from the solids.

The reaction product consists of E-isomers and Z-isomers.* If nitriles in which $R^1$ is hydrogen are used, the 3-alkoxynitrile will contain small amounts of the acetal formed by addition of the reaction alcohol $R^2OH$, and of a compound containing the moiety $R^3$ in position 2 due to alkylation.
*According to the JUPAC rules Z means the former designation cis-isomer and E-isomer formerly being designated as trans-isomer.

The acetal can be cleaved to the desired 3-alkoxyacrylonitrile by adding mineral acids such as $H_3PO_4$, $H_2SO_4$ or HCl or acid salts or mineral acids such as $KHSO_4$, while it is being worked up. At the same time, this will transpose the Z-isomer to the more stable E-isomer.

The alkylation product is separated by fractional distillation. It is desirable that the moieties $R^2$ and $R^3$ be the same.

EXAMPLES

Example 1

In a two-liter autoclave with a lifting stirrer, carbon monoxide is injected at a CO pressure of 40 bar and a temperature of 60° C. into a mixture of 1100 g of acetonitrile, 102.0 g (1.5 mol) of sodium ethoxide, 55.5 g (0.75 mol) of Ca(OH)$_2$ and 5.1 g of triethylamine, until 30 minutes later no more carbon monoxide was absorbed. Then, at standard pressure, 193.5 g (3.0 mol) of ethyl chloride is added and the suspension is stirred for 6 hours at 120° C. Then the solid is removed by filtration, washed with acetonitrile, and the combined filtrates are fractionally distilled. At standard pressure, a mixture of formic acid ester, alcohol, acetonitrile and a remainder of the ethyl chloride is distilled out. The residue is fractionally distilled in vacuo. 119.6 g of distillate boiling from 80° to 92° C. (13 Torr) is obtained as product. Composition, determined by gas chromatography: 82.3 Fl.-% (Z/E)-3ethoxypropenenitrile (A), 9.0 Fl.-% 3,3-diethoxypropanenitrile (B) and 8.7 Fl.-% (Z/E)-3-ethoxy-2-ethylpropenenitrile (C).

The total amount of (A) and (B), reckoned as (A), gives a yield of 73.4% with respect to the alcoholate.

Example 2

Same as Example 1, but with 1000 g of acetonitrile; the reaction is performed with carbon monoxide. After the addition of the ethyl chloride at 120° C., the suspension obtained was distilled with thorough mechanical stirring.

122 g of distillate is obtained:
(A)=57.8 Fl.-%*
(B)=31.9 Fl.-%
(C)=7.8 Fl.-%

Yield of (A) composed of (A) and (B): 70.1% with respect to the alcoholate.
*which is equivalent to volume-%

Example 3

Same as Example 1, but using 2.9 of tetra-n-butylammonium chloride instead of triethylamine. 119.0 g of distillate is obtained (83.2 Fl.-% (A), 8.5 Fl.-% (B) and 8.3 Fl.-% (C)). Yield: 72.8% with respect to the alcoholate.

Example 4

Same as Example 1, but using 245.1 g (2.25 mol) of ethyl chloride. The product is 104.3 g of distillate (74.1 Fl.-% (A), 16.7 Fl.-% (B) and 9.2 Fl.-% (C)). The yield, reckoned as (A), amounts to 61.2% with respect to the alcoholate.

Example 5

Same as the procedure of Example 1, but using 81.0 g (1.5 mol) of sodium methoxide. The alpha-formyl sodium salt is produced at 70° C. and 50 bar CO, and reacted with 151.5 g (3.0 mol) of methyl chloride as in Example 1. In the distillation, 89.5 g of distillate is obtained, boiling from 64° to 81° C. at 12 Torr (gas chromatographic analysis; 78.5 Fl.-% (Z/E)-3-methoxy-propenenitrile, 17.6 Fl.-% 3,3-dimethoxypropanenitrile and 3.7 Fl.-% (Z/E)-3-methoxy-2-methyl-propenenitrile). Yield: 66.0%, reckoned as 3-methoxy-propionitrile, with respect to the alcoholate.

EXAMPLE 6

Example 1 is repeated, but 1100 g of propionitrile was reacted. Instead of acetonitrile, at 75° C. and 50 bar CO pressure. The vacuum distillation yields 121.4 g of distillate boiling from 81° to 99° C. at 12 Torr (93.2 Fl.-% (Z/E)-3-ethoxy-2-methyl-propenenitrile and 6.6 Fl.-% 3,3-diethoxy-2-methyl-propanenitrile). Yield: 71.3% with respect to the alcoholate.

Example 7

As in Example 6, 1000 g of propionitrile is reacted with 81.0 g (1.5 mol) of sodium methoxide at 80° C. with CO at 50 bar pressure, and reacted with 151.5 g (3.0 mol) of methyl chloride. The vacuum distillation yields 100.8 g of distillate (boiling from 68° to 73° C. at 12 Torr). Yield: 69.3% (Z/E)-3-methoxy-2-methyl-propenenitrile, with respect to the alcoholate.

Example 8

A reaction mixture as in Example 1 containing 1000 g of butyronitrile is made to react at 85° C. with carbon monoxide of 45 bar pressure, and transposed as in Example 1 with 193.5 g (1.5 mol) of ethyl chloride. Product: 122.0 g of distillate (boiling from 87° to 106° C. at 12 Torr). Yield: 65.0%, calculated as 3-ethoxy-2-ethyl-propenenitrile.

It will be understood that the specification and examples are illustrative but not limitative of the present invention and that other embodiments within the spirit and scope of the invention will suggest themselves to those skilled in the art.

What is claimed is:

1. A method of preparing 3-alkoxy-acrylonitriles of the formula $$R^3O-CH=C(R^1)-C\equiv N, \quad \text{I}$$

wherein

R$^1$ is H; straight-chain or branched alkyl moieties of 1 to 20 carbon atoms; straight-chain or branched moieties —(CH$_2$)$_n$—CN, —(CH$_2$)$_n$OR$^4$ or —(CH$_2$)$_n$—CH(OR$^4$)$_2$ wherein n=0 to 5, and R$^4$ is alkyl; and R$^3$ is straight-chain or branched alkyl or alkenyl moieties with 1 to 12 carbon atoms, the moieties —(CH$_2$)$_p$—OR$^4$ with p=1 to 5 and R$^4$ with the above meaning;

comprising reacting a compound of the formula $$R^1-CH_2-CN \quad \text{II,}$$

which serves as both starting material and solvent wherein R$^1$ has the above meaning, with an alcoholate of the formula $$M(OR^2)_m \quad \text{III,}$$

wherein M is an alkali metal with m=1 or an alkaline earth metal with m=2 and R$^2$ is a straight-chain or branched alkyl moiety of 1 to 5 carbon atoms, and with carbon monoxide at elevated pressure of at least about 5 bar and a temperature of 20° to 220° C. to form the corresponding alpha-formyl alkali or alkaline earth salt of compound II; and reacting the resulting salt at a temperature of about 20° to about 220° C. with a halogen compound of the formula $$R^3\text{-Hal} \quad \text{IV,}$$

wherein R$^3$ has the above-given meaning and Hal represents chlorine, bromine or iodine.

2. The method of claim 1, wherein a stabilizer is included in the reaction mixture and comprises a basically reacting compound of the alkali or alkalne earth metals.

3. The method of claim 1, wherein a catalyst is used and comprises a tertiary amine or quaternary ammonium salt.

4. The method of claim 3, wherein there is used 1 to 10 wt.-% of catalyst, with respect to the amount of alcoholate.

5. The method of claim 1, wherein the reaction temperature is maintained between 60° and 120° C.

6. The method of claim 1, wherein the reaction temperature for the reaction with the substances of the formula R$^3$-Hal is run at temperatures between 60° and 220° C.

7. The method of claim 6 wherein the temperature range is 90° to 150° C.

8. The method of claim 1 wherein the temperature of the reaction with carbon monoxide is in the range of 35° to 100° C.

* * * * *